(12) United States Patent
Caldironi

(10) Patent No.: US 6,402,774 B1
(45) Date of Patent: Jun. 11, 2002

(54) METHOD AND APPARATUS FOR DYNAMIC EXPOSURE TO ULTRAVIOLET RAYS

(75) Inventor: Franco Caldironi, Cunardo (IT)

(73) Assignee: Biophoenix S.R.L., Milan (IT)

( * ) Notice: Subject to any disclaimer, the term of this patent is extended or adjusted under 35 U.S.C. 154(b) by 131 days.

(21) Appl. No.: 09/627,326

(22) Filed: Jul. 27, 2000

(30) Foreign Application Priority Data

Aug. 6, 1999 (IT) .......................................... MI99A1794

(51) Int. Cl.$^7$ ................................................. A61N 1/00
(52) U.S. Cl. ............................. 607/91; 607/88; 607/94; 250/494.1; 128/898
(58) Field of Search .................. 607/88–95; 250/494.1, 250/498.1, 504 R; 128/898

(56) References Cited

U.S. PATENT DOCUMENTS 4,974,922 A * 12/1990 Mori .......................... 350/96.1
5,957,959 A * 9/1999 Rissmaney et al. ........... 607/88

* cited by examiner

Primary Examiner—Linda C. M. Dvorak
Assistant Examiner—Ahmed Farah
(74) Attorney, Agent, or Firm—Young & Thompson

(57) ABSTRACT

A method and apparatus for dynamic exposure to ultraviolet rays; a person is radiated by means of ultraviolet ray sources, at high and/or low UV pressure, emitted by radiation units peripherally arranged around a footboard on which the person to be radiated is standing upright on a rotary platform of the footboard which it is allowed to slowly rotate. Reflecting panels, opposite to the UV radiation units, allow the UV rays to be radiated directly and by reflection, to reduce energy consumption.

13 Claims, 2 Drawing Sheets

METHOD AND APPARATUS FOR DYNAMIC EXPOSURE TO ULTRAVIOLET RAYS

BACKGROUND OF THE INVENTION

The present invention relates to a method and apparatus for dynamic exposure to ultraviolet rays emitted by radiating units positioned around a person in an upright condition.

In particular the invention is directed to a method and an irradiation apparatus suitable for phototherapy treatments, tests of light triggering by means of ultraviolet rays, which allow even irradiation of the body surface, for cosmetic tanning treatments and for other similar applications.

In phototherapy treatments and, more generally, in treatments of the human body by means of ultraviolet rays, use of cabins and/or radiating apparatus positioned in front of or all around a person to be radiated, who remains immobile in standing position, is well known, and whereby a static distribution of the radiating energy emitted by special UV lamps is obtained on all or part of the surface of the body.

The use of static radiating systems, whereby a given portion or the whole surface to be irradiated remains fixed and constantly facing the source of radiation, entails limits and definite disadvantages both as regards the method of exposure to the ultraviolet rays, and as regards the efficiency of the same radiation apparatus.

In particular, a fixed position of the person in front of a UV ray source, may entail excessive absorption of radiation with possible negative consequences on the cells which become excessively stimulated by the radiating energy, due to the difficulty in portioning the distribution of the rays and in obtaining an even "pressure" or load of the same rays on the surface exposed during irradiation.

It must also be borne in mind that, in the case of conventional static systems, such as cabins or radiating panels, frequency generators have to be used which have specific properties according to the type of exposure to ultraviolet rays (UV) to be performed, that is to say according to whether phototherapy at high or low UV pressure, or the mixed type, is to be performed.

For these reasons a conventional apparatus is extremely complex and expensive, and in some cases somewhat bulky, difficult to remove or to position in a given area.

With this apparatus of the known type it is possible to vary the quantity of irradiated energy only by adjusting the power and the time of radiation during which a person has to remain still in front of the radiating panels or inside an irradiation cabin.

OBJECT OF THE INVENTION

The main object of the present invention is to provide a new system for dynamic exposure to ultraviolet rays which provides a dynamic energy radiating action as opposed to conventional static apparatus.

More particularly, an object of the invention is to provide a method and apparatus suitable for allowing dynamic distribution of the radiating energy, whereby it is possible to obtain an even metering of UV rays on the exposed skin surface.

Yet a further object of the invention is to provide a method and apparatus as defined above, whereby it is possible to obtain a gradual pressure of the ultraviolet rays, with alternating steps of increasing and decreasing UV ray pressure, at appropriate time intervals.

An additional object of the invention is to provide a method and apparatus for skin radiation with UV rays which allow a drastic reduction in the consumption of electrical energy or in the power.

BRIEF DESCRIPTION OF THE INVENTION

The objects and advantages referred above can be achieved by means of a method for the exposure of the skin of a person to an ultraviolet ray source in accordance with the invention, in which an exposed skin surface of the person to be treated is radiated by means of ultraviolet rays emitted by radiation units peripherally arranged, to the same person, in which at least part of the skin surface of the person is radiated by maintaining the same person in an upright position and by allowing the same to slowly move or rotate in relation to the radiation units during the treatment.

According to another aspect of the invention, an apparatus has been provided for the dynamic exposure of a person to an ultraviolet ray source, comprising a plurality of radiation units around the person to be radiated, said apparatus comprising:

- a footboard provided with a rotary platform or table for supporting the person in an upright position;
- drive means to cause a slow rotation of the support platform;
- said rotary platform being provided with a peripheral hand grip to allow the person standing on the platform to maintain a stable upright position on the same platform during rotation thereof.

The various radiation units consist of simple radiating panels or composite panels, varyingly movable or positionable around the platform supporting the person during UV treatment. In this respect the individual units or individual radiating panels are supported by wheels.

According to another aspect of the invention, it is possible to use, in combination with the UV radiating units, a number of UV reflecting panels positioned in front of and/or appropriately placed at an angle in relation to the units for the emission of UV rays, in order to diffuse the UV rays by reflection, over the entire skin surface of a body, maintaining the emission points at a minimum.

According to another aspect of the invention, it is possible to modify or change the type of UV exposure simply by replacing some or all of the radiating panels with others having UV emission lamps of different type and/or with radiating units of different shape and dimensions, while maintaining a person in the upstanding condition on a rotary platform of the support footboard.

The same arrangement of the reflecting panels can be rapidly changed or eliminated, by orienting or arranging the same panels differently, or by moving them away from the support footboard.

BRIEF DESCRIPTION OF THE DRAWINGS

These and further features of the UV radiating method and apparatus according to the present invention, will be made clearer by the following description with reference to the example of the accompanying drawings in which.

DETAILED DESCRIPTION OF THE INVENTION

Figure 1:
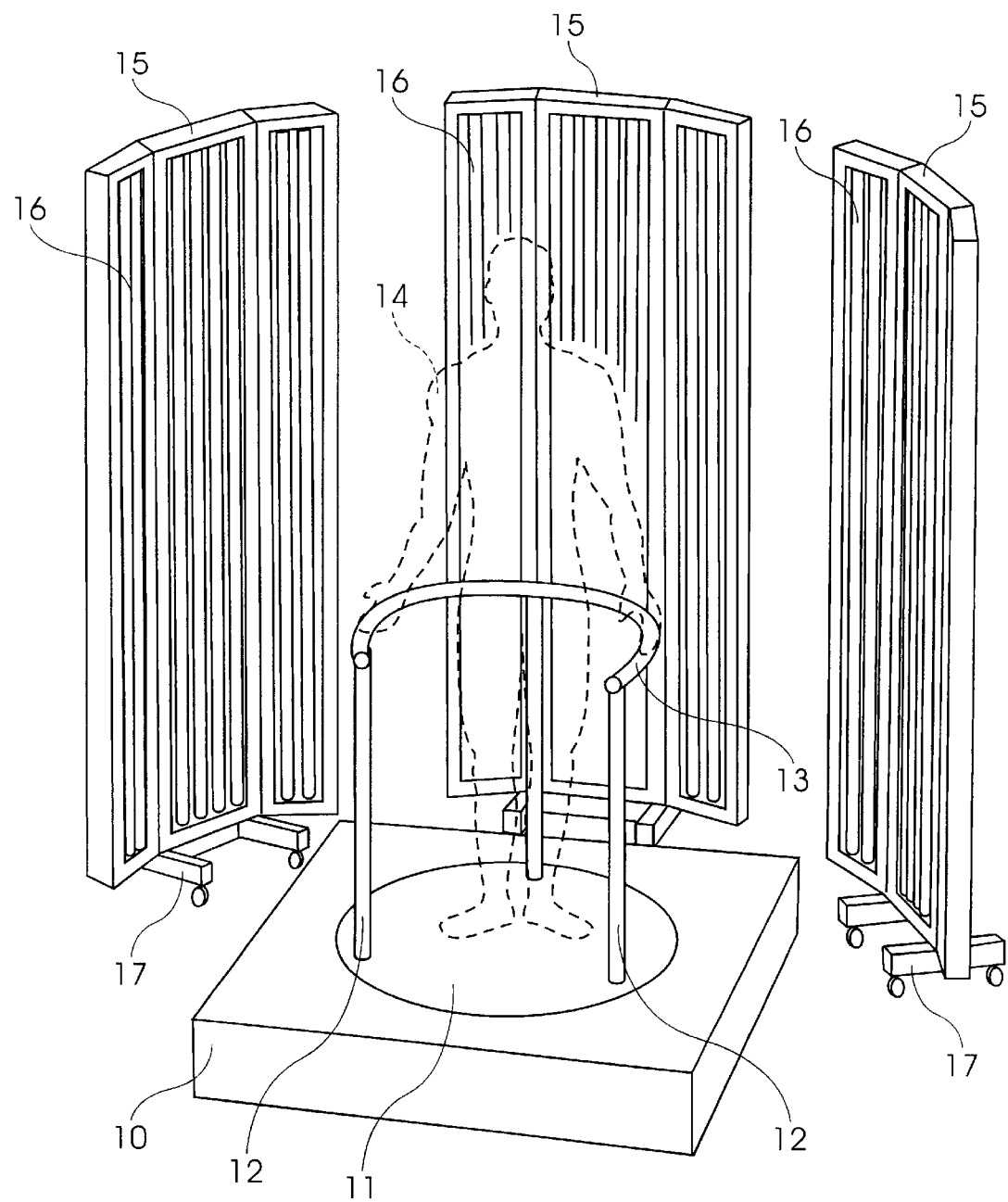
FIG. 1 is a perspective view of apparatus according to the invention.

The apparatus of FIG. 1 comprises a footboard 10, for example with a square shape, provided with a rotary platform or table 11 which is slowly rotated in a controlled mode.

The rotary platform 11 is provided with a suitable hand grip to allow a stable upright position for a person 14 standing on the same platform. These hand grip can be performed in any way to consist, for example, of three uprights 12 which support a handrail 13 to form a peripheral guard which the person 14 can grip with the hands.

Several UV radiation sources of the same or different type are positionable peripherally around the platform 12; for example the UV sources may be formed by varyingly shaped panels 15, each provided with UV radiating lamps 16, suitable for emitting UV rays in a predetermined range of frequencies.

Each UV radiating panel or group of radiating panels 15 is positioned next to the footboard 10 in a movable manner, for example by supporting the panels 15 by carriages 17 provided with castor wheels.

The radiating panels 15 can be arranged around the entire periphery of the footboard 10 or, as shown in FIG. 1, around one or more sides of the same footboard.

Figure 2:
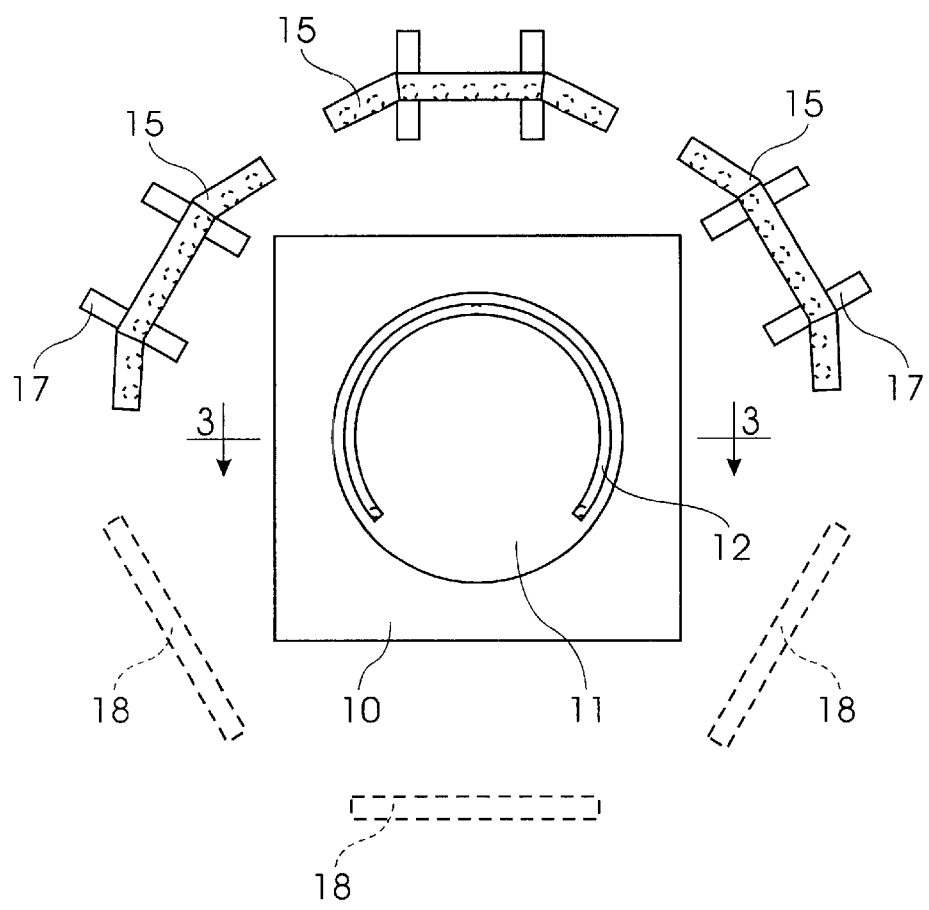
FIG. 2 is a top view of the apparatus of FIG. 1 with the addition of some UV reflecting panels.

In combination with the UV radiating panels 15, as shown in the top view of FIG. 2, it is also possible to use UV reflecting panels 18, provided for example by mirrors or by suitable UV reflecting surfaces, positioned in front of and at a certain angle in relation to the radiating panels 15.

The use of UV reflecting surfaces, in combination with UV radiating panels around part of the periphery of the footboard 10, allows the dual advantage of radiating evenly the entire surface of the body 14, reducing the number of radiating panels and, as a result, the consumption of electrical energy.

Figure 3:
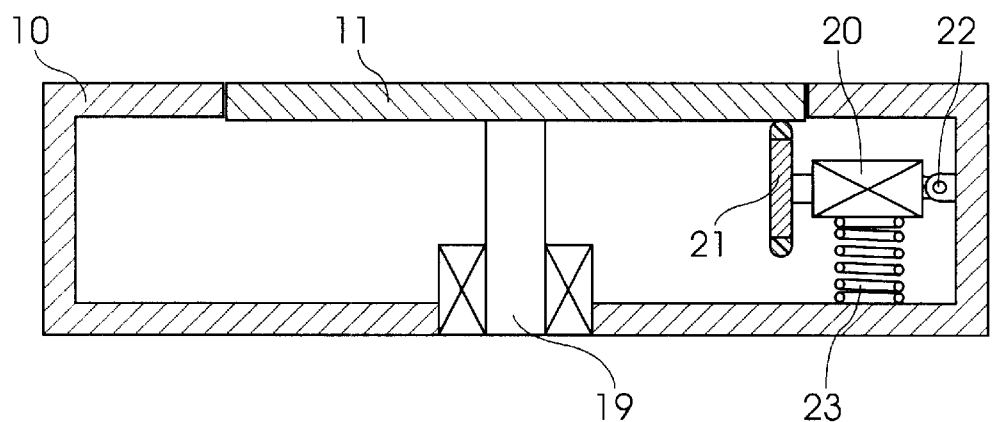
FIG. 3 is a cross-sectional view of the footboard with rotary platform of the apparatus of FIG. 1.

The footboard 10 with the rotary platform 11 can be shaped in any suitable manner; for example, as shown in FIG. 3, the footboard 10 can be in the form of a box-like body comprising platform 11, rotatingly supported by a vertical axis 19.

The rotary platform 11 is driven to rotate by a friction wheel 21, connected to the shaft of an electric drive motor 20. The electric motor 20 is tiltably supported and is subjected to the action of biasing device which pushes the friction wheel 21 against the lower surface of the rotary platform 11. For example, as shown, the electric motor 20 can be hinged in 22 and subjected to the thrust of a helical spring 23; other solutions are obviously possible in relation to the scope of the invention.

The UV exposure method and use of the apparatus described above is briefly the following:

it is assumed that the platform 11 is at a standstill and that a person 14 to be radiated is standing on the footboard, holding firmly to the handrail 13.

At this point, by means of a control panel (not shown), the motor 20 is actuated and, by means of the friction wheel 21, drives rotation of the platform 11 whereon the person 14 to be radiated is positioned.

The platform 11 is made to rotate very slowly, both to allow the required metering of UV rays on the exposed skin surface to be radiated, in relation to the power of radiation supplied and the exposure time, and to prevent the person 14 from losing his or her balance and accidentally falling from the same rotating platform.

By way of an example the platform 11 can be made to rotate at 1 to 5 rpm, preferably between 1 and 2.5 rpm.

During slow rotation of the platform 11, the entire uncovered skin surface of the person 14 is gradually and repeatedly exposed to the UV rays emitted by the radiating panels 15, in order to achieve even portioning and distribution of the UV rays on the same exposed skin surface.

According to another aspect of the invention, it is possible to control and change the pressure of the ultraviolet radiation and the quantity of radiation supplied, gradually and intermittently, by alternating steps of greater radiation power with intermediate steps of reduced radiation, thanks to the cyclical exposure of the skin surface to UV ray sources by rotation, or by stopping the rotation of the platform for a predetermined period of time, or again by varying the rotational speed of the platform, all this in a controlled mode by an appropriate programmable control unit, which controls management of the entire apparatus.

The advantages of the method and of the apparatus according to the invention are numerous: in particular, as already explained, it is possible to obtain a dynamic distribution of the radiated energy over all or part of the exposed skin surface, obtaining an interactive effect of the UV energy load, and consequent advantages for metabolic stimulation of the cells with pigmentation functions.

The individual skin cells are no longer charged constantly and statically with. the radiated energy, in that there are now radiation steps alternating with absence or reduction of radiation due to rotation of the person 14, and hence the possibility of improved exploitation of the same apparatus for the type of exposure to be performed.

Moreover, in respect of previously known static systems, a drastic reduction in the energy consumption is achieved in that the supply of UV light energy is adequately reduced without negatively influencing or reducing the efficacy of the exposure to the UV rays.

The highly innovative aspect of the present invention thus consists in subjecting the exposed skin surface of a person to be radiated, to a repeated alternation of exposures to UV rays, slowly moving the person to be radiated by rotating the same in relation to the radiating source.

The slow rotation also allows an even distribution and improved dosing of the UV rays, in relation to the previously known static systems in which the skin surface to be treated was subjected to a specific and constant UV light pressure, with all the negative effects which may arise therefrom on the radiated skin.

Contrarily, according to the invention, the skin surface is repeatedly subjected to periods of irradiation and to periods of rest, further exploiting in this way the receptive capacity of the UV rays.

At the end of the exposure, after a programmed period of time, the platform 11 stops, allowing the person 14 to alight without any danger.

From what has been said and shown with reference to the accompanying drawings, it will therefore be clear that a new method and new apparatus for UV radiation exposure have been provided, particularly suitable for treatments with UV rays at high and/or low pressure.

In all cases a method and apparatus have been provided which are extremely effective, capable of improving performances of UV treatments without negative effects on the skin surface, also allowing a consistent reduction in energy consumption without affecting the efficacy of the apparatus.

The intent however is that what has already been said and illustrated in the accompanying drawings has been given purely by way of a non-limiting example of the invention.

I claim:

1. Method for dynamic exposure of the skin surface of a person in which the exposed skin surface is subjected to ultraviolet rays emitted by UV sources peripherally positioned around a radiation area on which said person upstands, comprising the steps of cyclically radiating at least part of the exposed skin surface, by maintaining said person in an upright position and rotating the same person in relation to the UV ray source.

2. Method according to claim 1, comprising alternating steps of radiation and reduction of the UW rays energy while said person is slowly rotating in respect to the UV ray source.

3. Method according to claim 1, in which radiation of the skin surface is partially performed, by reflection of the UV rays emitted by the UV ray source.

4. Method according to claim 1, in which dosing of the UV rays is performed by changing the rotational speed of the person in respect to the UV ray source.

5. Method according to claim 1, comprising the step of maintaining the person in slow rotation in respect to the UV ray source.

6. Method according to claim 5, in which rotation is comprised between 1 and 5 rpm.

7. Method according to claim 6, in which rotation is between 1 and 2.5 rpm.

8. Apparatus for ultraviolet ray treatment, with a plurality of UV ray sources peripherally positioned around a radiation area, said apparatus comprising:

a footboard provided with a rotary platform for supporting a person to be radiated;

drive means to cause slow rotation of the support platform; and in which the rotary platform is provided with a and grip.

9. Apparatus according to claim 8, wherein said hand grip comprises a peripheral guard which extends upwards, along at least a portion of the peripheral edge of the platform.

10. Apparatus according to claim 8, wherein said UV ray source is of the movable type.

11. Apparatus according to claim 10, wherein said UV ray source is supported by a carriage having castor wheels.

12. Apparatus according to claim 8, comprising a plurality of UV radiating panels extending along a portion of the peripheral of the footboard.

13. Apparatus according to claim 12, further comprising a plurality of UV ray reflecting panels peripherally arranged along at least a portion of the peripheral of the footboard, in opposition to the UV radiating panels of the UV ray source.

* * * * *